(12) United States Patent
Seaman et al.

(10) Patent No.: US 11,154,504 B2
(45) Date of Patent: Oct. 26, 2021

(54) SUSTAINED RELEASE CYCLOSPORINE-LOADED MICROPARTICLES

(71) Applicant: MIDATECH PHARMA (WALES) LIMITED, Cardiff South Glamorgan (GB)

(72) Inventors: Paul Seaman, Cardiff (GB); Katharine Bamsey, Cardiff (GB); Nigel Thomas, Cardiff (GB); Dewi Paice, Cardiff (GB)

(73) Assignee: MIDATECH PHARMA (WALES) LIMITED, Cardiff South Glamorgan (GB)

( * ) Notice: Subject to any disclaimer, the term of this patent is extended or adjusted under 35 U.S.C. 154(b) by 0 days.

(21) Appl. No.: 15/780,208

(22) PCT Filed: Dec. 16, 2016

(86) PCT No.: PCT/EP2016/081593
§ 371 (c)(1),
(2) Date: Nov. 8, 2018

(87) PCT Pub. No.: WO2017/103218
PCT Pub. Date: Jun. 22, 2017

(65) Prior Publication Data
US 2019/0054023 A1    Feb. 21, 2019

(30) Foreign Application Priority Data

Dec. 18, 2015  (GB) ...................................... 1522441

(51) Int. Cl.
| A61K 9/16 | (2006.01) |
| A61K 9/00 | (2006.01) |
| A61K 47/26 | (2006.01) |
| A61K 47/38 | (2006.01) |
| A61K 31/00 | (2006.01) |
| A61K 38/13 | (2006.01) |
| A61K 47/10 | (2017.01) |
| A61K 9/10 | (2006.01) |

(52) U.S. Cl.
CPC .......... *A61K 9/1647* (2013.01); *A61K 9/0019* (2013.01); *A61K 9/0051* (2013.01); *A61K 9/1694* (2013.01); *A61K 31/00* (2013.01); *A61K 38/13* (2013.01); *A61K 47/10* (2013.01); *A61K 47/26* (2013.01); *A61K 47/38* (2013.01); *A61K 9/10* (2013.01)

(58) Field of Classification Search
CPC .. A61K 9/1647; A61K 9/0019; A61K 9/0051; A61K 9/1694; A61K 31/00; A61K 38/13; A61K 47/10; A61K 47/26; A61K 47/38; A61K 9/10
See application file for complete search history.

(56) References Cited

U.S. PATENT DOCUMENTS

| 2003/0147954 | A1 | 8/2003 | Yang et al. | |
| 2004/0092435 | A1 | 5/2004 | Peyman | |
| 2008/0097335 | A1* | 4/2008 | Trogden ................ | A61F 9/0017 604/192 |
| 2009/0202642 | A1* | 8/2009 | Huang .................. | A61K 9/0024 424/488 |
| 2010/0273721 | A1* | 10/2010 | Belichard .............. | A61K 38/57 514/20.8 |
| 2015/0342872 | A1* | 12/2015 | Williamson ......... | A61K 9/0019 424/490 |

FOREIGN PATENT DOCUMENTS

| CN | 101437478 | 5/2009 |
| CN | 104623630 | 5/2015 |
| EP | 1484054 | 12/2004 |
| JP | 2015025735 | 2/2015 |
| WO | 1996031202 | 10/1996 |
| WO | WO 03063841 | 6/2005 |
| WO | WO 2009/130319 | 10/2009 |
| WO | 2010111449 | 9/2010 |
| WO | WO 2011/061297 | 5/2011 |
| WO | 2012042273 | 4/2012 |
| WO | 2012042274 | 4/2012 |
| WO | WO 2012042273 | 4/2012 |
| WO | 2016011449 | 1/2016 |
| WO | 2017103113 | 6/2017 |

OTHER PUBLICATIONS

Webb. Interpretation of Particle Size Reported by Different Analytical Techniques. , Micromeritics Instrument Corp. 2006, 10 pages. (Year: 2006).*
Horiba Scientific. A Guidebook To Particle Size Analysis, ed. Horiba Instruments Inc. 2017, 34 pages. (Year: 2017).*
Copland et al., (2008) "The Clinical Time-Course of Experimental Autoimmune Uveoretinitis Using Topical Endoscopic Fundal Imaging with Histologic and Cellular Infiltrate Correlation", Invest. Opthalmol. Vis. Sci., 49(12):5458-5465.
Sánchez et al., (1993) "Development of biodegradable microspheres and nanospheres for the controlled release of cyclosperin A", Int. J. Pharmaceutics, 99:263-271.

(Continued)

*Primary Examiner* — Robert A Wax
*Assistant Examiner* — Olga V. Tcherkasskaya
(74) *Attorney, Agent, or Firm* — Rudy J. Ng; Carol L. Francis; Bozicevic, Field & Francis LLP

(57) ABSTRACT

A controlled release pharmaceutical formulation is provided, comprising cyclosporine-loaded microparticles of a bioresorbable polymer comprising poly(D,L-lactide), wherein the mean diameter of the microparticles is in the range 20 μm to 40 μm. Also provided are medical uses of the pharmaceutical formulation, in particular in the treatment of uveitis, a process for production of the pharmaceutical formulation and injectable dosage forms, including those formulated for intravitreal injection.

28 Claims, 6 Drawing Sheets

(56) References Cited

OTHER PUBLICATIONS

Li et al., (2005) "In vitro and in vivo studies of cyclosporin A-loaded microspheres based on copolymers of lactide and ϵ-caprolactone: Comparison with conventional PLGA microspheres", Int. J. Pharmaceutics, 295:67-76.

Yuan He et al., (2006) "Cyclosporine-Loaded Microspheres for Treatment of Uveitis In Vitro Characterization and In Vivo Pharmacokinetic Study", Investigative Opthalmology & Visual Science, 47(9):3983-3988.

* cited by examiner

SUSTAINED RELEASE CYCLOSPORINE-LOADED MICROPARTICLES

CROSS-REFERENCE TO RELATED APPLICATIONS

This application is the National Stage of International Application No. PCT/EP2016/081593, filed Dec. 16, 2016, which claims benefit under 35 U.S.C. § 119(d) of United Kingdom application serial number GB1522441.3, filed Dec. 18, 2015, all of which applications are incorporated herein by reference in their entireties.

FIELD OF THE INVENTION

The present invention relates to controlled release pharmaceutical formulations containing cyclosporine encapsulated within biocompatible polymeric microparticles for use in medicine, including for use in the treatment of uveitis. Processes for production of the microparticles and delivery systems are also disclosed.

BACKGROUND TO THE INVENTION

The present invention is directed at compositions and products, and methods of making and administering such compositions and products, including for the treatment of eye disorders in mammals and particularly humans.

WO2012/042273 and WO2012/042274 describe apparatus and process for the preparation of solid beads that encapsulate a bioactive agents and which are suitable for use in sustained release, e.g., via depot injection.

EP1484054 describes a drug delivery system for the subconjunctival administration of fine grains.

Copland et al., *Invest. Opthalmol. Vis. Sci.*, 2008, Vol. 49, No. 12, pp. 5458-5465, describes the clinical time-course of Experimental Autoimmune Uveoretinitis (EAU) using topical endoscopic fundal imaging (TEFI) with histologic and cellular infiltrate correlation.

He et al., *Invest. Ophthalmol. Vis. Sci.*, 2006, Vol. 47, pp. 3983-3988, describes cyclosporine-loaded microspheres for the treatment of uveitis.

WO2016/011449 was published 21 Jan. 2016 and describes suspension compositions of cyclosporine A for subconjunctival and periocular injection.

WO96/31202 describes a controlled release pharmaceutical formulation comprising cyclosporine entrapped in a biodegradable polymer to form microspheres or nanospheres such that the cyclosporine is substantially in an amorphous state and the biodegradable polymer comprises greater than 12.5% w/w poly(lactide).

Li et al., *Int. J. Pharmaceutics*, 2005, Vol. 295, pp. 67-76, describes in vitro and in vivo studies of cyclosporine A-loaded microspheres based on copolymers of lactide and ε-caprolactone in comparison with PLGA microspheres.

Sanchez et al., *Int. J. Pharmaceutics*, 1993, Vol. 99, pp. 263-273, describes the development of biodegradable microspheres and nanospheres for the controlled release of cyclosporin A.

US2004/0092435 describes a method for treatment of ocular disease with cyclosporine A.

WO2010/111449 describes intraocular sustained release drug delivery systems and methods for treating ocular conditions.

There remains an unmet need for pharmaceutical formulations and delivery systems for use in the treatment of uveitis, particularly those which reduce or minimise the frequency and/or discomfort of intravitreal injection. The present invention addresses these and other needs.

BRIEF DESCRIPTION OF THE INVENTION

Broadly, the present invention relates to controlled or sustained release pharmaceutical formulations of cyclosporine for intravitreal injection, e.g., for treatment of uveitis. The present inventors have surprisingly found that a highly monodisperse microsphere formulation of around 20-40 μm diameter formed of poly(lactide) encapsulating cyclosporine exhibits superior intravitreal injectability in comparison with known cyclosporine-loaded microsphere formulations. Moreover, data from an in vivo murine model of autoimmune uveitis indicate efficacy similar to that of systemic cyclosporine administration, but with a much more locally defined site of action and therefore fewer off-target effects are expected.

Accordingly, in a first aspect the present invention provides a controlled release pharmaceutical formulation comprising cyclosporine-loaded microparticles of a bioresorbable polymer comprising poly(D,L-lactide), wherein the mean diameter of the microparticles is in the range 20 μm to 40 μm, for example 25 μm to 36 μm. In some cases, at least 95% of the microparticles of the formulation have a diameter in the range 25 μm to 40 μm.

In some cases the bioresorbable polymer comprises poly (D,L-lactide) and poly(L-lactide). The poly(L-lactide) is preferably at least partially in crystalline form. It is believed that having a proportion of crystalline poly(L-lactide) in the polymer matrix in addition to the non-crystalline poly(D,L-lactide) contributes to a slower rate of degradation in vivo and thereby extends the period of sustained release of the cyclosporine payload in comparison with microparticle formulations of pure poly(D,L-lactide), lacking crystalline poly (L-lactide). In some cases, the polymer comprises between 1% and 15% w/w poly(L-lactide).

In some cases the bioresorbable polymer comprises poly (D,L-lactide) and poly(D,L-lactide-co-glycolide) and may optionally also include poly(L-lactide). The ratio of lactide to glycolide co-monomers in the final mixture of polymers ("the L:G ratio") may influence the rate of bioresorption and therefore the release characteristics of the cyclosporine over time. In certain cases, the L:G ratio may be in the range 60:40 to 95:5, for example within the range 70:30 to 80:20.

In some cases the microparticles of the invention comprise between 15% and 25% w/w cyclosporine. In particular, the cyclosprorine loading may be in the range 17% to 21% (w/w).

In some cases, the coefficient of variation of the diameter of the microparticles is 0.1 or less (e.g. 0.05, 0.01 or 0.001 or less), the coefficient of variation being the standard deviation of the diameter of the microparticles divided by the mean diameter of the microparticles. The present inventors have found that a monodisperse formulation, i.e. the microparticles being essentially all the same or very similar size and substantially spherical geometry and therefore having a low coefficient of variation of microparticle diameter, contributes to improved injectability through the narrow gauge needles employed in administration by intravitreal injection. Without wishing to be bound by any particular theory, it is presently believed that the relatively loose packing of identically sized spheres, in comparison with the relatively tighter packing of irregularly sized or shaped microparticles, leads to a reduction in viscosity and in needle blockage during injection.

In some cases, the standard deviation of the diameter of the microparticles is less than 3.0 µm, for example in the range 1.0 µm to 3.0 µm.

In some cases the microparticles have a "healed" surface. Healing in this context refers to a smooth surface achieved by heating the formed microparticle, in a post-production process, to a temperature just below the glassification temperature or "glass transition temperature" ($T_g$) of the polymer. Heating the microparticle in this way causes the surface temporarily to adopt a molten or rubber-like state in which the polymer flows so as to fill in and/or smooth surface deformations yielding a smooth surface. Upon subsequent cooling, the smooth surface is retained. Microparticles having a healed surface exhibit slower release of pharmaceutical payload because the irregular or microporous surface is rendered smooth, which tends to retain payload entrapped in the microparticle interior in comparison with the non-healed microparticle with a relatively more porous and irregular surface.

In some cases the formulation further comprises a pharmaceutically acceptable carrier, diluent, vehicle, buffer, anti-agglomeration agent and/or viscosity modifier. In some cases, the formulation comprises said microparticles suspended in a liquid vehicle, which liquid vehicle has a viscosity of between 30 and 45 mPas measured at 17° C. or as measured at 20° C. Viscosity measurements may be as determined using an A&D SV-1a Vibroviscometer (A&D Instruments Ltd, Abingdon, UK) according to the manufacturer's instructions. As described in Example 5 herein, it was found that a liquid vehicle having a viscosity in this range helps to maintain microparticles in suspension for a length of time suitable for injection while avoiding significant difficulties in syringeability. In certain cases, the microparticles may be suspended in a liquid injection vehicle that exhibits shear-thinning and/or thixotropic behaviour. In other words the viscosity of the fluid is lower under a shear stress than in the absence of a shear stress. As described in detail herein, the shear-thinning behaviour advantageously retains the microparticles in suspension for a period of time (e.g. several minutes), yet the drop in viscosity under the shear stress of injection through a narrow intravitreal needle facilitates injection, e.g. by reducing the mechanical ejection force required. In certain cases, the formulation of the present invention comprises a thixotropic agent. In some cases, the thixotropic agent is selected from the group consisting of: hypromellose, hydroxyethyl cellulose, hydrophillically-modified hydroxyethyl cellulose, Xanthan Gum, Guar Gum, and Cetyl alcohol.

In particular, the pharmaceutically acceptable carrier, diluent or vehicle may comprise one or more of: a salt, a surfactant, a sugar, and sterile water. In certain cases, the formulation of the invention may further comprise one or more (e.g. 2, 3, 4, 5, 6, 7, 8, or more) of: polysorbate 20, polysorbate 80, phosphate buffered saline, sucrose, carboxymethyl cellulose, hydroxyethyl cellulose, hypromellose, hydroxyethyl cellulose, hydrophillically-modified hydroxyethyl cellulose, Xanthan Gum, Guar Gum, Cetyl alcohol, and mannitol.

In some cases, the formulation further comprises: phosphate buffered saline, polysorbate 80, hydroxyethyl cellulose and hypromellose, and optionally mannitol.

In some cases, the concentration of the formulation components are in the respective concentration ranges as follows:
(i) phosphate buffer saline: 5.0 to 8.0 mg/mL, e.g. 6.5 mg/mL;
(ii) polysorbate 80: 0.8 to 1.2 mg/mL, e.g. 1.0 mg/mL;
(iii) hydroxyethyl cellulose: 1.8 to 2.2 mg/mL, e.g. 2.0 mg/mL;
(iv) hypromellose: 3.8 to 4.2 mg/mL, e.g. 4.0 mg/mL;
(v) mannitol, when present: 4.8 to 5.2 mg/mL, e.g. 5.0 mg/mL; and/or
(vi) said cyclosporine-loaded microparticles: 100 to 200 mg/mL, e.g. 125 mg/mL or 150 mg/mL.

The formulation of the invention may be in injectable form or adapted to be reconstituted into injectable form prior to use. Preferably, the formulation is for intravitreal depot injection. The formulation may be provided in the form of a single injectable dose, wherein the injection volume is compatible with intravitreal injection.

In some cases, the formulation may be injectable through a 30 gauge, 0.5 inch length hypodermic needle (inner diameter of 0.159±0.019 mm; length 25.4 mm) at a recovery percentage of at least 80%, at least 85% or at least 90%. As shown in Table 1 herein, injection recovery percentages above 90% have been demonstrated for certain embodiments of the formulation of the present invention.

In a second aspect the present invention provides a controlled release pharmaceutical formulation of the first aspect of the invention for use in medicine.

In a third aspect the present invention provides a controlled release pharmaceutical formulation of the first aspect of the invention for use in the treatment of uveitis in a mammalian subject (e.g. a human or a horse).

In some cases the mammalian subject has been diagnosed with, or is suspect of having uveitis. In certain cases, the uveitis is sight-threatening intermediate, posterior or pan-uveitis of non-infectious aetiology or is equine uveitis, e.g. equine recurrent uveitis. The treatment may be intended to reduce or prevent uveitis recurrence in a subject undergoing steroidal uveitis treatment. In certain cases the uveitis may be sight threatening tuberculosis uveitis (i.e. uveitis that is secondary to infection with *Mycobacterium tuberculosis*). In particular, the treatment may be combined with antibiotic therapy for treatment of the underlying tuberculosis infection. Antibiotic treatment of tuberculosis may, for example, involve treatment with isoniazid and/or rifampicin.

In accordance with the first, second or third aspect of the invention the formulation may be for administration via intravitreal injection. The formulation may, for example, be for administration by weekly injection, two-weekly injection, three-weekly, four-weekly injection, monthly injection, six-weekly injection, eight-weekly injection, two-monthly injection, 12-weekly injection, three-monthly injection, 16-weekly injection or four-monthly injection.

In a fourth aspect, the present invention provides a method of treating uveitis in a mammalian subject (e.g. a human or a horse), comprising administering a controlled release pharmaceutical formulation of the first aspect of the invention to the subject in need of therapy. In some cases, the uveitis may be sight-threatening intermediate, posterior or pan-uveitis of non-infectious aetiology. In certain cases, the uveitis may be equine uveitis, e.g., equine recurrent uveitis (also known as moon blindness). In certain cases, the method of treatment may, or may be intended to, reduce or prevent uveitis recurrence in a subject undergoing steroidal uveitis treatment. In some cases, method may be for treating sight threatening tuberculosis uveitis. The method may further comprise administering antibiotic therapy to the subject for treatment of tuberculosis infection. In some cases, the controlled release pharmaceutical formulation is administered to the subject via intravitreal injection.

In a fifth aspect, the present invention provides use of controlled release pharmaceutical formulation of the first aspect of the invention in the preparation of a medicament for use in a method of the fourth aspect of the invention.

In a sixth aspect, the present invention provides an article of manufacture comprising:
- a controlled release pharmaceutical formulation of the first aspect of the invention;
- a container for housing the formulation; and
- an insert or label. The insert and/or label provides instructions, dosage and/or administration information relating to the use of the formulation in the treatment of uveitis in a mammalian subject.

In a seventh aspect, the present invention provides a process for producing a controlled release pharmaceutical formulation of the first aspect of the invention, comprising:
providing a first liquid comprising a solute, a solvent and cyclosporine or a salt, solution or suspension thereof, the solute comprising a poly(D,L-lactide)-containing polymer, the concentration of polymer in the first liquid being at least 10% w/v, 'w' being the weight of the polymer and 'v' being the volume of the solvent;
providing a liquid droplet generator comprising a piezoelectric component operable to generate liquid droplets,
causing the liquid droplet generator to form liquid droplets of the first liquid;
passing the liquid droplets through a gas,
contacting the liquid droplets with a second liquid so as to cause the solvent to exit the droplets, thus forming solid microparticles;
the solubility of the solvent in the second liquid being at least 5 g of solvent per 100 ml of second liquid, the solvent being substantially miscible with the second liquid,
wherein the second liquid is provided as a flow and the method comprises contacting the liquid droplets with the flow of second liquid.

In some cases, the process may be as described in co-pending application PCT/EP2016/081436, filed 16 Dec. 2016, published 22 Jun. 2017 as International Application Publication No. WO/2017/103113, which claims priority to GB1522423.1, filed 18 Dec. 2015, the entire contents of which are expressly incorporated herein by reference.

In some cases, the solvent may comprise dimethyl sulfoxide (DMSO).

In some cases, the second liquid comprises water. In particular, the second liquid may comprise an alcohol in water, such as tert-butanol in water.

In some cases, the temperature of the first liquid in the vicinity of the liquid droplet generator is in the range 10° C. to 25° C.

In some cases, the temperature of the second liquid is in the range 1° C. to 10° C.

In some cases, the concentration of polymer in the first liquid is at least 30% w/v.

In certain cases in accordance with this aspect of the invention, the process further comprises collecting the solid microparticles by separating the solid microparticles from the second liquid.

In some cases, the process further comprises collecting the solid microparticles and formulating or packaging the microparticles into a pharmaceutical composition or delivery form. In particular,
the solid microparticles may be formulated into a liquid for delivery by intravitreal injection.

In certain case, the process of the seventh aspect of the invention further comprises freeze-drying the microparticles to form a lyophilized population of the microparticles. In particular, the microparticles may be freeze-dried with one or more excipients, for example the one or more excipients may include mannitol. In some cases, the process may further comprise a reconstitution step in which the dry microparticles (e.g. lyophilized microparticles) are mixed with a liquid injection vehicle to form a suspension suitable for injection. The liquid injection vehicle may be as defined in connection with the first aspect of the invention.

In an eighth aspect, the present invention provides a process for producing an injectable formulation of active-containing (e.g. cyclosporine-loaded) microparticles, comprising:
providing a dry population of active-containing (e.g. cyclosporine-loaded) microparticles;
bringing the microparticles into contact with an injection vehicle solution comprising: phosphate buffered saline, polysorbate 80, hydroxyethyl cellulose and hypromellose, and optionally mannitol.

In some cases, the concentration of the components of the injection vehicle are in the respective concentration ranges as follows:
phosphate buffer saline: 5.0 to 8.0 mg/mL, e.g. 6.5 mg/mL;
polysorbate 80: 0.8 to 1.2 mg/mL, e.g. 1.0 mg/mL;
hydroxyethyl cellulose: 1.8 to 2.2 mg/mL, e.g. 2.0 mg/mL;
hypromellose: 3.8 to 4.2 mg/mL, e.g. 4.0 mg/mL; and
mannitol, when present: 4.8 to 5.2 mg/mL, e.g. 5.0 mg/mL.

The cyclosporine-loaded microparticles may, in some cases, be combined with the injection vehicle to give a concentration in suspension (w/v) of 100 to 200 mg/mL, e.g. 125 mg/mL or 150 mg/mL. In some cases, the injection vehicle has a viscosity of between 30 and 45 mPas measured at 20° C. In some cases, the injection vehicle displays thixotropic and/or shear-thinning behaviour.

In some cases, the cyclosporine-loaded microparticles are as defined in connection with the first aspect of the invention.

In accordance with the present invention, particularly the second to fifth aspects thereof, the subject may be a human, a companion animal (e.g. a dog or cat), a laboratory animal (e.g. a mouse, rat, rabbit, pig or non-human primate), a domestic or farm animal (e.g. a pig, cow, horse or sheep). Preferably, the subject is a human. Uveitis is known to affect horses. Equine recurrent uveitis is the most common form of blindness in horses. Treatment of equine subjects with the compositions of the present invention is specifically contemplated.

The present invention includes the combination of the aspects and preferred features described except where such a combination is clearly impermissible or is stated to be expressly avoided. These and further aspects and embodiments of the invention are described in further detail below and with reference to the accompanying examples and figures.

DETAILED DESCRIPTION OF THE INVENTION

Figure 1:
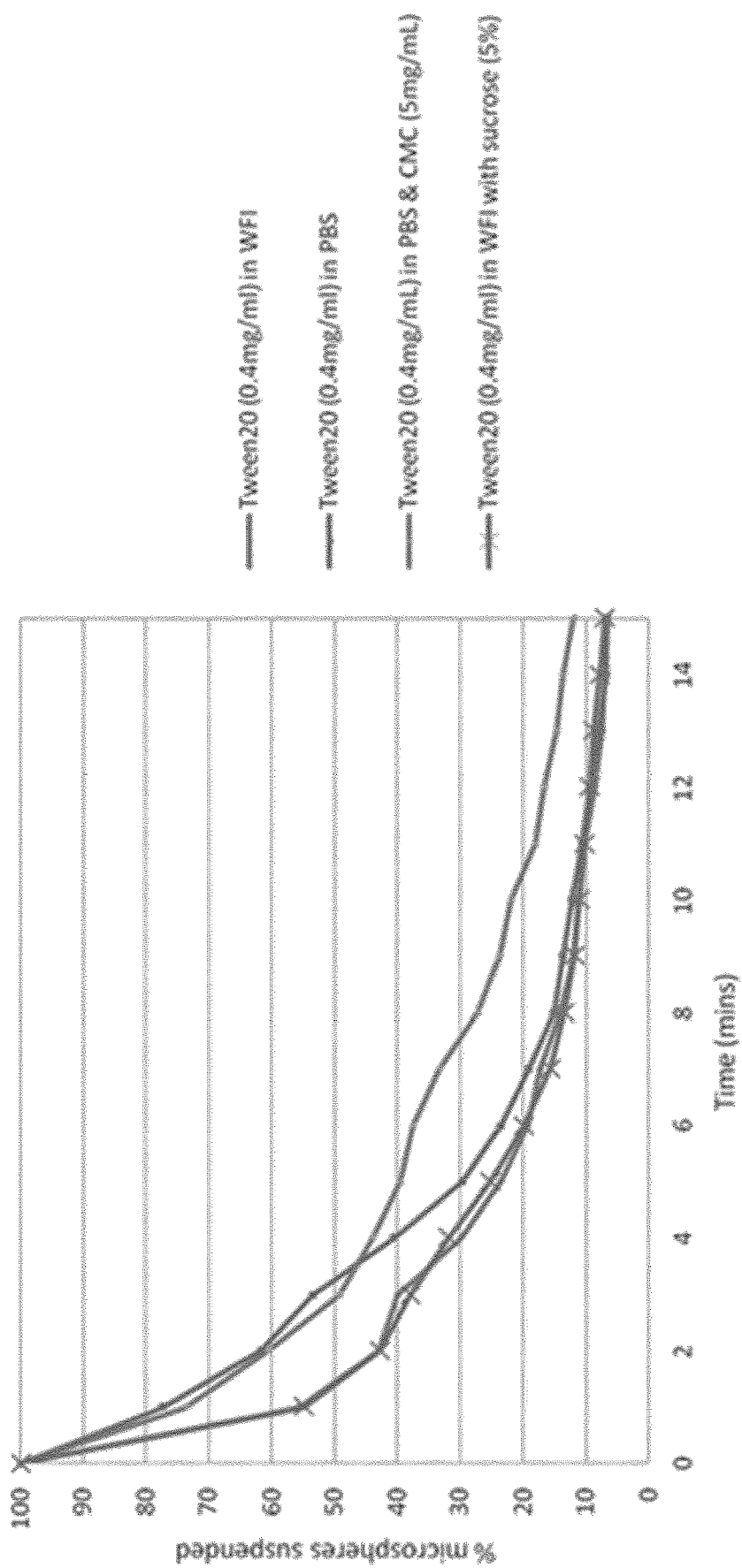
FIG. 1 shows microsphere settling following suspension in a range of injection vehicles. The settling rate is plotted (percentage microspheres suspended vs. time) for each of four formulations: Tween20 (0.4 mg/ml) in WFI (blue); Tween20 (0.4 mg/ml) in PBS (red); Tween20 (0.4 mg/ml) in PBS and CMC (5 mg/ml) (green); and Tween20 (0.4 mg/ml) in WFI with sucrose (5%) (purple).

In describing the present invention, the following terms will be employed, and are intended to be defined as indicated below.

Microparticles

Microparticles in accordance with the present invention may be in the form of solid beads. As used herein in connection with microparticles or beads, solid is intended to encompass a gel. Microparticles as used herein specifically include any polymeric particle or bead of micron scale (typically up to 999 µm in diameter). Microparticles contemplated herein advantageously include the monodisperse polymeric beads obtainable by the process described in WO 2012/042274 (the entire contents of which are expressly incorporated herein by reference—see, e.g., claims 1 to 44 thereof).

Cyclosporine ("CsA")

Ciclosporin (International Nonproprietary Name; INN), also known as cyclosporine, cyclosporine, ciclosporin A, cyclosporine A, cyclosporine A or "CsA" is a cyclic nonribosomal peptide of 11 amino acids that has immunosuppressant activity. CsA has the IUPAC name (3 S,6S,9S,12R, 15S,18S,21S,24S,30S,33 S)-30-Ethyl-33-[(1R,2R,4E)-1-hydroxy-2-methyl-4-hexen-1-yl]-6,9,18,24-tetraisobutyl-3, 21-diisopropyl-1,4,7,10,12,15,19,25,28-nonamethyl-1,4,7, 10,13,16,19,22,25,28,31-undecaazacyclotritriacontane-2,5, 8,11,14,17,20,23,26,29,32-undecone. CsA exhibits poor solubility in water and has been marketed in suspension, emulsion and gelatin capsule formulations.

Process for Encapsulating Cyclosporine within Microparticles

In certain cases the microparticles may be produced by the process described in WO2012/042274 (the entire contents of which are expressly incorporated herein by reference). In some cases, the microparticles may be produced by the process described in co-pending application PCT/EP2016/081436, filed 16 Dec. 2016 and/or GB1522423.1, filed 18 Dec. 2015, the entire contents of which are both expressly incorporated herein by reference. In particular, the cyclosporine may be added as the "target material" to the first liquid, the first liquid being a polymer comprising poly(D,L-lactide) dissolved in a solvent (e.g. DMSO). The second liquid may be a mixture of water and an alcohol (e.g. tert-butanol) and is provided in the form of a jet. The first liquid is ejected from a plurality of liquid droplet generators (e.g. an inkjet printhead having a bank of 100-1500 outlets) to form liquid droplets that pass through a gas and into the jet of the second liquid. The solvent then exits the droplets as it passes into the second liquid resulting in the formation of solid polymeric microparticles in which cyclosporine is encapsulated. It has been found that this production method results in cyclosporine-encapsulated microparticles of small size (20-40 µm diameter) with excellent uniformity of size (e.g. coefficient of variation of 0.1 or less). The combination of small size and uniformity of size has been found to improve the injectability of the microparticles through the narrow gauge needles (e.g. 27G) necessary for intravitreal injection as compared with cyclosporine-loaded microparticles of larger size and/or less monodisperse character. In particular, prior-described methods of production, such as emulsion-based or solvent evaporation techniques, typically result in larger microparticles with larger variability of size (see, e.g., Table 1 of He et al., *Invest. Ophthalmol. Vis. Sci.*, 2006, Vol. 47, pp. 3983-3988).

Administration and Treatment

The microparticles and pharmaceutical formulations of the invention may be administered to patients by any number of different routes. However it is specifically contemplated herein that administration is via intravitreal depot injection.

The CsA-loaded microparticles of the present invention may be for use in the treatment of uveitis. In particular, the treatment of uveitis may be one or more of the following:

1. Prevention of recurrence of sight-threatening intermediate, posterior or pan-uveitis of non-infectious aetiology in patients in whom conventional therapy with prolonged high dose steroids (systemically or topically administered) is required.

The present inventors believe that use of the CsA-loaded microparticles of the present invention may reduce the number and/or severity of recurrences avoiding the use of large doses of systemic steroids or systemic immunosuppressing medication (e.g. oral CsA).

2. Treatment of sight-threatening intermediate, posterior or pan-uveitis of non-infectious aetiology.

The present inventors believe that use of the CsA-loaded microparticles of the present invention as first line treatment, would provide benefits in the form of reduced side effects (non-systemic delivery) and reduced dosing frequency, thereby improving patient experience and compliance.

3. Treatment of sight-threatening tuberculosis (TB) uveitis.

The present inventors believe that use of the CsA-loaded microparticles of the present invention to treat the ocular manifestations of the TB and prevent the ocular sequelae of chronic uveitis. Advantageously, treatment with the CsA-loaded microparticles of the present invention may be carried out in combination with antibiotic therapy for the treatment of the underlying TB infection.

The following is presented by way of example and is not to be construed as a limitation to the scope of the claims.

EXAMPLES

Example 1—Encapsulation of Cyclosporine (CsA) within Polymeric Microspheres

The following formulation was used in the synthesis of CsA-encapsulated microspheres:
For 1 mL
150 mg Resomer R202H (poly(D,L-lactide) acid terminated, MW 18000-24000)
150 mg Resomer RG752H (Poly(D,L-lactide-co-glycolide) acid terminated, lactide:glycolide 75:25, MW 4000-15000)
75 mg Ciclosporin A
q.s. ad DMSO Synthesis was performed using a piezoelectric droplet generator device as described in WO2012/042273 and/or as in co-pending application PCT/EP2016/081436, filed 16 Dec. 2016, published 22 Jun. 2017 as International Application Publication No. WO/2017/103113, which claims priority to GB1522423.1, filed 18 Dec. 2015, the entire contents of which are expressly incorporated herein by reference. In brief, the first liquid was made up of the above combination of Resomer R202H, Resomer RG752H and Ciclosporin A, dissolved in DMSO. The second liquid was a mixture of water and an alcohol (e.g. tert-butanol), which was provided in the form of a flow in a channel or in the form of a jet. The first liquid is ejected from a plurality of liquid droplet generators to form liquid droplets that pass through a gas (e.g. air) and into the flow of the second liquid (within the channel or into the jet, respectively). The solvent then exits the droplets as it passes into the second liquid resulting in the formation of solid polymeric microparticles in which cyclosporine is encapsulated.

A total mass of 1.5 g of microspheres was produced, these had a drug loading of 20.2%. The microspheres were then post-processed in a batch process as follows:
Wash medium=5 mg/mL mannitol
Wash temperature=37° C.
Duration of wash=1 hour Drug loading in the final product was 20.1%, indicating minimal drug loss during post-processing.

All microspheres were stored at 2-8° C.

Batch Analysis Results

| Test | Specification | Results |
| --- | --- | --- |
| Appearance | White to off-white powder | White to off-white powder |
| Appearance on reconstitution | White to off-white homogenous suspension, free from visible aggregates | White to off-white homogenous suspension, free from visible aggregates |
| Reconstitution time | <3 mins | Pass |
| Identity | Profile and retention times to be qualitatively similar to reference | Pass |
| Assay (rpHPLC) | 18-22% w/w Ciclosporin A | 20.1% w/w Ciclosporin A |
| Particle size | Report result. Target 26-30 μm | 28.24 μm(StDev = 3.3) |
| pH on reconstitution | For report | 7.04 |
| Biological Methods | | |
| Sterility (PhEur) | Pass | Not tested (non-sterile batch) |
| Endotoxin (PhEur) | Pass | Not tested (non-sterile batch) |

The injection vehicle constituents were as follows:
5 mg/mL Sodium carboxymethylcellulose
0.4 mg/mL Polysorbate-20
Phosphate buffered solution, pH 7

Batch Analysis Results

| Test | Specification | Results |
| --- | --- | --- |
| Appearance | Clear, colourless liquid | Clear, colourless liquid |
| pH | For report | 7.1 |
| Density | For report | 1.01 g/mL |
| Biological Methods | | |
| Sterility (PhEur) | Pass | Not tested |
| Endotoxin (PhEur) | Pass | Not tested |

Example 2—Development of Injection Vehicle and Assessment of Injectability

Due to the intravitreal route and nature of CsA-loaded microspheres, injection vehicle optimization was undertaken in order to provide simple and repeatable injection. A large number of studies have been performed by the present inventors looking at the reconstitution time, settling rate and injectability of placebo microspheres—for these purposes, placebo microspheres have highly similar properties to CsA-loaded. Initial investigations have looked at the buffer system, surfactant content, polyol content and viscosity modifiers. These experiments have enabled the present inventors to establish a preferred resuspension and injection protocol. Homogenous suspensions can be formed in ≤2 minutes and have been optimised to provide a satisfactory settling rate, FIG. 1, and data obtained thus far indicate that these are injectable through ½" 30G needles, Table 1.

TABLE 1

Recovery of encapsulated cyclosporine ("OpsiSporin") following ejection from a 30 G ½" hypodermic needle.

| Sample # | Needle size | % Recovery |
| --- | --- | --- |
| 1 | 30 G/0.5" | 92.9 |
| 2 | 30 G/0.5" | 90.4 |
| 3 | 30 G/0.5" | 98.0 |

Example 3—Investigation into the Syringeability of Five Different Cyclosporine-Loaded Microsphere Batches Through a Range of Hypodermic Needles Method Five microsphere batches used in this investigation and their properties are described in Table 2.

TABLE 2

Properties of Microsphere Batches 1-5:

| Microsphere batch # | Drug loading (%w/w) | Average size (μm) | Standard deviation | % CV |
|---|---|---|---|---|
| Vial 1 - 231-114-001 | 21.0 | 55.76 | 3.77 | 6.76 |
| Vial 2 - 231-180-003 | 18.0 | 35.69 | 2.83 | 7.93 |
| Vial 3 - 231-105 + 180 | 20.4 | 41.86 | 8.98 | 21.45 |
| Vial 4 - 231-108-001 | 20.5 | 52.25 | 4.46 | 8.54 |
| Vial 5 - 231-175-001 | 19.3 | 53.18 | 5.39 | 10.14 |

Preparation of OpsiSporin Injection Vehicle

The injection vehicle consisted of phosphate buffered saline (pH 7) with 0.8 μg/mL tween$_{20}$ and 5 mg/mL sodium carboxymethylcellulose.

Syringeability

The syringeability of microsphere batches was examined at a concentration of 18, 36, 54, 72 and 140 mg/mL. In particular, a specific mass of microspheres was weighed into a 2 mL Eppendorf tube, 1 mL of injection vehicle (described above) added and the Eppendorf tubes placed in a sonicator for 1 minute. This resulted in a homogenous suspension, of which 100 μL was drawn into a 1 mL syringe mounted with either a 21G, 25G, 27G or 30G hypodermic needle. The suspension was then ejected through the same hypodermic needle.

To be considered a pass, the correct volume of suspension must have been both aspirated into and ejected from the syringe. In ability to aspirate, needle blockage or incorrect delivery of the dose were considered failures.

Results

The results are shown in Tables 3 to 7, using Yes (✓) or No (✗) to identify whether the aspiration and injection at each concentration was possible. Three consecutive failures (indicated by "✗") confirmed the suspension was not injectable.

TABLE 3 syringeability of 100 μL of a microsphere suspension at a concentration of 18 mg microspheres/mL

| Microsphere batch | 21 G | 25 G | 27 G | 30 G |
|---|---|---|---|---|
| Vial 1 231-114-001 | ✓ | ✓ | ✓ | ✓ |
| Vial 2 231-180-003 | ✓ | ✓ | ✓ | ✓ |
| Vial 3 231-105 + 180 | ✓ | ✓ | ✓ | ✓ |
| Vial 4 231-108-001 | ✓ | ✓ | ✓ | ✗ |
| Vial 5 231-175-001 | ✓ | ✓ | ✓ | ✗ |

TABLE 4 syringeability of 100 μL of a microsphere suspension at a concentration of 36 mg microspheres/mL

| Microsphere batch | 21 G | 25 G | 27 G | 30 G |
|---|---|---|---|---|
| Vial 1 231-114-001 | ✓ | ✓ | ✓ | ✗ |
| Vial 2 231-180-003 | ✓ | ✓ | ✓ | ✓ |
| Vial 3 231-105 + 180 | ✓ | ✓ | ✓ | ✓ |
| Vial 4 231-108-001 | ✓ | ✓ | ✓ | ✗ |
| Vial 5 231-175-001 | ✓ | ✓ | ✓ | ✗ |

TABLE 5 syringeability of 100 μL of a microsphere suspension at a concentration of 54 mg microspheres/mL

| Microsphere batch | 21 G | 25 G | 27 G | 30 G |
|---|---|---|---|---|
| Vial 1 231-114-00 | ✓ | ✓ | ✓ | ✗ |
| Vial 2 231-180-003 | ✓ | ✓ | ✓ | ✓ |
| Vial 3 231-105 + 180 | ✓ | ✓ | ✓ | ✓ |
| Vial 4 231-108-001 | ✓ | ✓ | ✓ | ✓ |
| Vial 5 231-175-001 | ✓ | ✓ | ✓ | ✗ |

TABLE 6 syringeability of 100 μL of a microsphere suspension at a concentration of 72 mg microspheres/mL

| Microsphere batch | 21 G | 25 G | 27 G | 30 G |
|---|---|---|---|---|
| Vial 1 231-114-001 | ✓ | ✓ | ✗ | ✗ |
| Vial 2 231-180-003 | ✓ | ✓ | ✓ | ✓ |
| Vial 3 231-105 + 180 | ✓ | ✓ | ✓ | ✗ |
| Vial 4 231-108-001 | ✓ | ✓ | ✓ | ✗ |
| Vial 5 231-175-001 | ✓ | ✓ | ✓ | ✗ |

TABLE 7 syringeability of 100 μL of a microsphere suspension at a concentration of 140 mg microspheres/mL

| Microsphere batch | 21 G | 25 G | 27 G | 30 G |
|---|---|---|---|---|
| Vial 1 231-114-001 | ✓ | ✓ | ✗ | ✗ |
| Vial 2 231-180-003 | ✓ | ✓ | ✓ | ✓ |
| Vial 3 231-105 + 180 | ✓ | ✓ | ✓ | ✗ |
| Vial 4 231-108-001 | ✓ | ✓ | ✓ | ✗ |
| Vial 5 231-175-001 | ✓ | ✓ | ✗ | ✗ |

Conclusions

Results from this experiment showed that CsA microspheres with a diameter of 35 μm and CV <10% could be aspirated and ejected through 27G and 30G hypodermic needles at suspension concentrations higher than larger and/or less monodisperse microsphere populations. This confirmed the diameter of microspheres and size distribution were critical to the microsphere suspension passing through the smallest hypodermic needles.

Example 4—In Vivo Treatment of Murine Model of Autoimmune Uveitis

Background to Experimental Model

The effectiveness of the cyclosporine-loaded microparticles of the present invention was evaluated using an established in vivo model of autoimmune uveitis. Copland et al., *Invest. Opthalmol. Vis. Sci.*, 2008, Vol. 49, No. 12, pp. 5458-5465 (incorporated herein by reference), describes the clinical time-course of Experimental Autoimmune Uveoretinitis (EAU) using topical endoscopic fundal imaging (TEFI) with histologic and cellular infiltrate correlation. The Copland paper employed a B10 mouse strain, whereas the present study employed a C57 mouse strain. It has been found that the B10 mouse strain exhibits are more acute disease, with a short duration and severe disease, whereas the C57 mouse strain exhibits a more long-lasting disease of lower severity. The present inventors selected the C57 mouse strain for the experimental murine model of autoimmune uveitis for the present study because its longer duration is better suited to evaluation of a sustained release, long-acting therapeutic product.

Experimental Outline

On arrival, the mice were randomly allocated to groups of 10 and allowed to acclimatise for one week. The health status of all animals was checked prior to start of the study.

In order to induce experimental autoimmune uveitis (EAU) on Day 0 animals were given a subcutaneous injection of the interphotoreceptor retinoid binding protein peptide 1-20 (IRBPp 1-20, GPTHLFQPSLVLDMAKVLLD (SEQ ID NO: 1); Severn Biotech.) antigen emulsified with Complete Freund's adjuvant (CFA; Sigma) (1:1 vol/vol) supplemented with 2.5 mg/ml *Mycobacterium tuberculosis* H37 Ra (Difco). Mice also received via i.p. injection, 1.5 µg *Bordetella pertussis* toxin (Calbiochem) at the time of immunisation.

Treatments were administered according to the schedule below (Table 8) in order to compare the efficacy of the sustained release with orally administered cyclosporine A and vehicle only control groups.

Due to the sustained release properties of the cyclosporine-loaded microparticle product ("OpsiSporin"), intravitreal treatment was administered on a single occasion only, day 0, following disease induction. A control group receiving vehicle only was also injected on day 0. In addition, two groups of 10 animals received CsA in CMC orally, once daily, as a positive control treatment.

Signs of clinical disease were monitored by topical endoscopic fundal imaging (TEFI) from day 7, twice weekly until termination day 28. Animals were also monitored twice weekly for signs of ill-health and weighed, any abnormalities were recorded.

TABLE 8

Treatment Groups and Dosages
All Groups were n = 10

| Group | Treatment | Route | Dose | 1st Dosing time/frequency |
|---|---|---|---|---|
| 1 | None | n/a | n/a | n/a |
| 2 | Injection vehicle | Intravitreal | n/a | Once on Day 0 |
| 3 | OpsiSporin | Intravitreal | 13.5 µg CsA | Once on Day 0 |
| 4 | OpsiSporin | Intravitreal | 4.5 µg CsA | Once on Day 0 |
| 5 | CsA in CMC | Oral | 20 mg/kg/day | s.i.d. from Day 0 |
| 6 | CsA in CMC | Oral | 6.7 mg/kg/day | s.i.d. from Day 0 | n/a—not applicable;
s.i.d.—single daily dose;
s.c.—subcutaneous;
i.p.—intraperitoneal;
IRBPp—interphotoreceptor retinoid binding protein peptide 1-20;
CFA—complete Freund's adjuvant;
CsA—cyclosporine A Intravitreal Injection volume was fixed at 4 µL, therefore to achieve the appropriate doses OpsiSporin suspensions were prepared as shown in Table 9.

TABLE 9

Microparticle suspensions

| Group | Target dose CsA | Microsphere drug loading | Dose of Q-Sphera microspheres | Microsphere Suspension | Injection Volume |
|---|---|---|---|---|---|
| 3 | 13.5 µg | 20.1% w/w | 67.1 µg | 16.8 mg/mL | 4 µL |
| 4 | 4.5 µg | 20.1% w/w | 22.4 µg | 4.6 mg/mL | 4 µL |

Readouts

Clinical Observations

Animals were weighed at the start of the study (Day 0), and then twice weekly until termination, day 28. All animals were also observed twice weekly for signs of ill health and any abnormalities recorded.

Retinal Imaging Using to Topical Endoscopic Fundal Imaging (TEFI)

Mouse retinas were scored twice weekly from day 7 until termination on day 28, following pupil dilation with Tropicamide 1%, followed by Phenylephrine hydrochloride 2.5%. Retinal images have been captured using Topical Endoscopic Fundal Imaging (TEFI) and scored according to the standardised scoring system below which gives a maximum score of 20 (Table 10).

TABLE 10

TEFI scoring

| Score | Optic disc | Retinal vessels | Retinal tissue Infiltration | Structural damage |
|---|---|---|---|---|
| 1 | Minimal inflammation | 1-4 mild cuffing's | 1-4 small lesions or 1 linear lesion | Retinal lesions or atrophy involving ¼ to ¾ of retinal area |
| 2 | Mild inflammation | >4 mild cuffing's or 1-3 moderate cuffing's | 5-10 small lesions or 2-3 linear lesions | Panretinal atrophy with multiple small lesions (scars) or ≤3 linear lesions (scars) |
| 3 | Moderate inflammation | >3 moderate cuffing's | >10 small lesions or >3 linear lesions | Panretinal atrophy with >3 linear lesions or confluent lesions (scars) |
| 4 | Severe inflammation | >1 severe cuffing's | Linear lesion confluent | Retinal detachment with folding |
| 5 | Not visible (white-out or severe detachment) | Not visible (white-out or severe detachment) | Not visible (white-out or severe detachment) | Not visible |

Results

Figure 2:
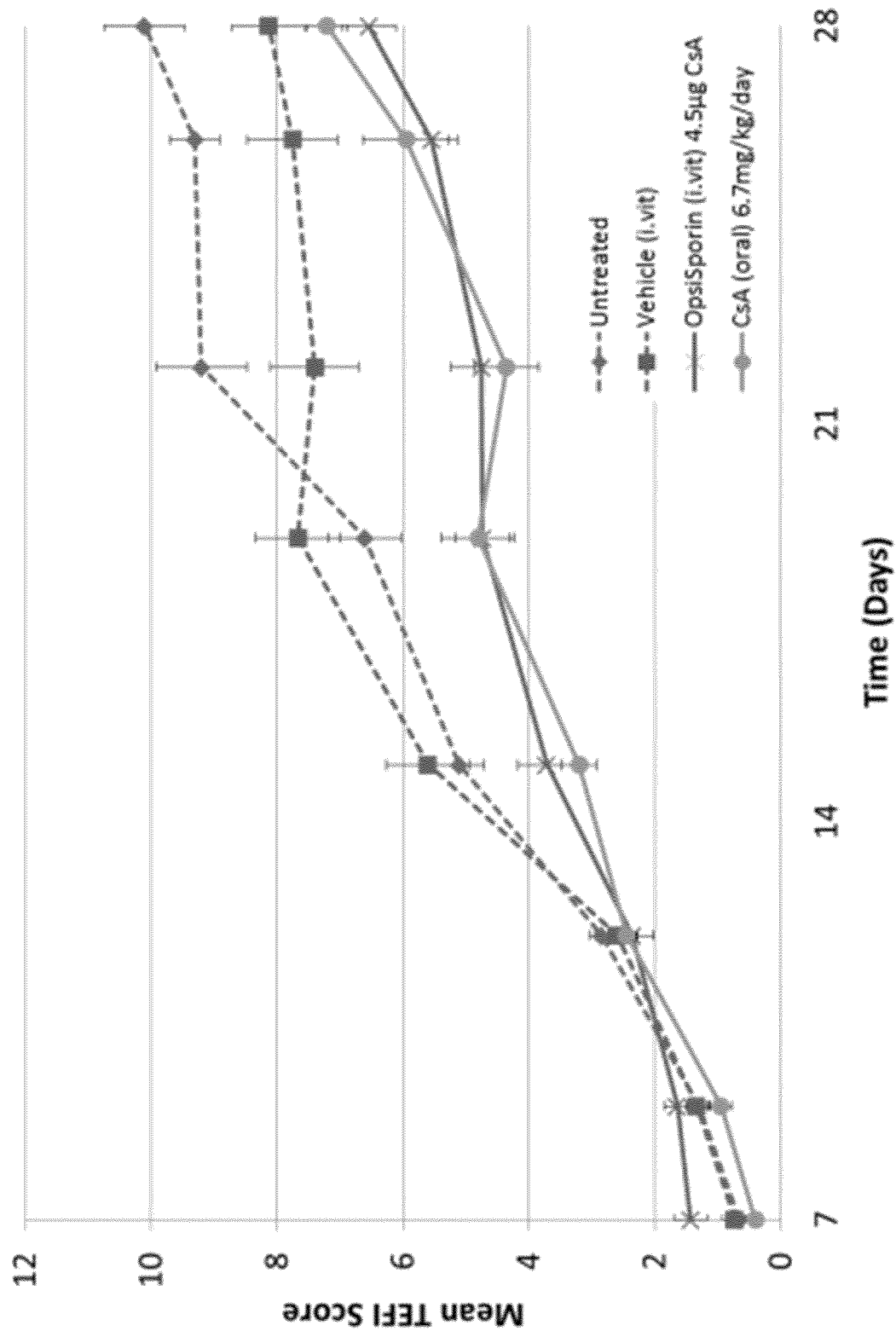
FIG. 2 shows a plot of uveitis disease severity scored by topical endoscopic fundal imaging (TEFI) over time in days for a murine model of uveitis untreated (diamonds), vehicle treated by intravitreal injection (squares), treated with 4.5 µg cyclosporine (CsA) in the form of CsA-loaded microparticles of the invention (crosses) and treated with 6.7 mg/kg/day oral CsA (circles). Both CsA-treated groups exhibited lower TEFI score (i.e. less severe disease) than untreated or vehicle.
Figure 3:
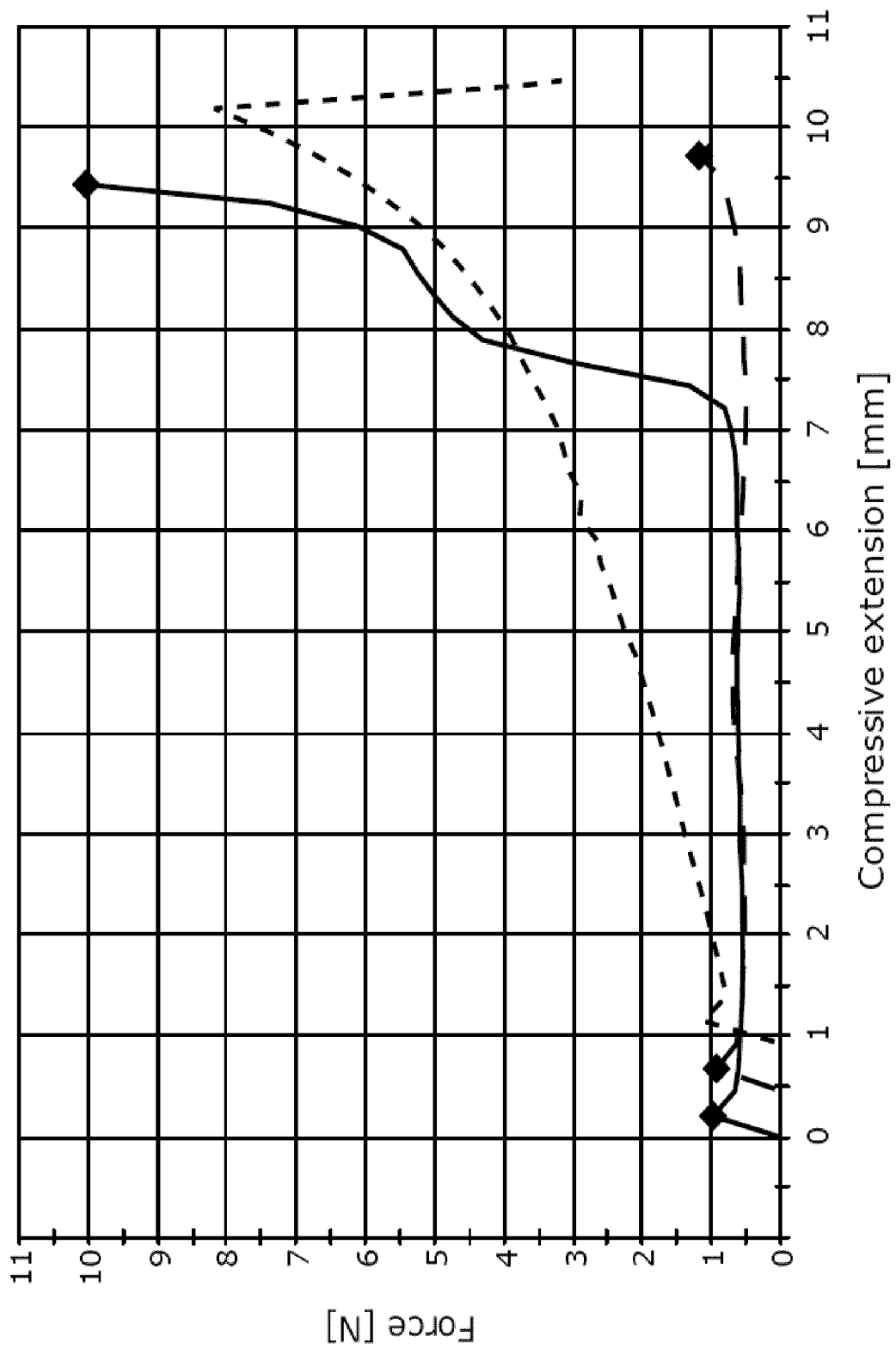
FIG. 3 shows an injectability plot of force (N) vs. compressive extension (mm) for the "current" injection vehicle as measured using the Instron device.
Figure 4:
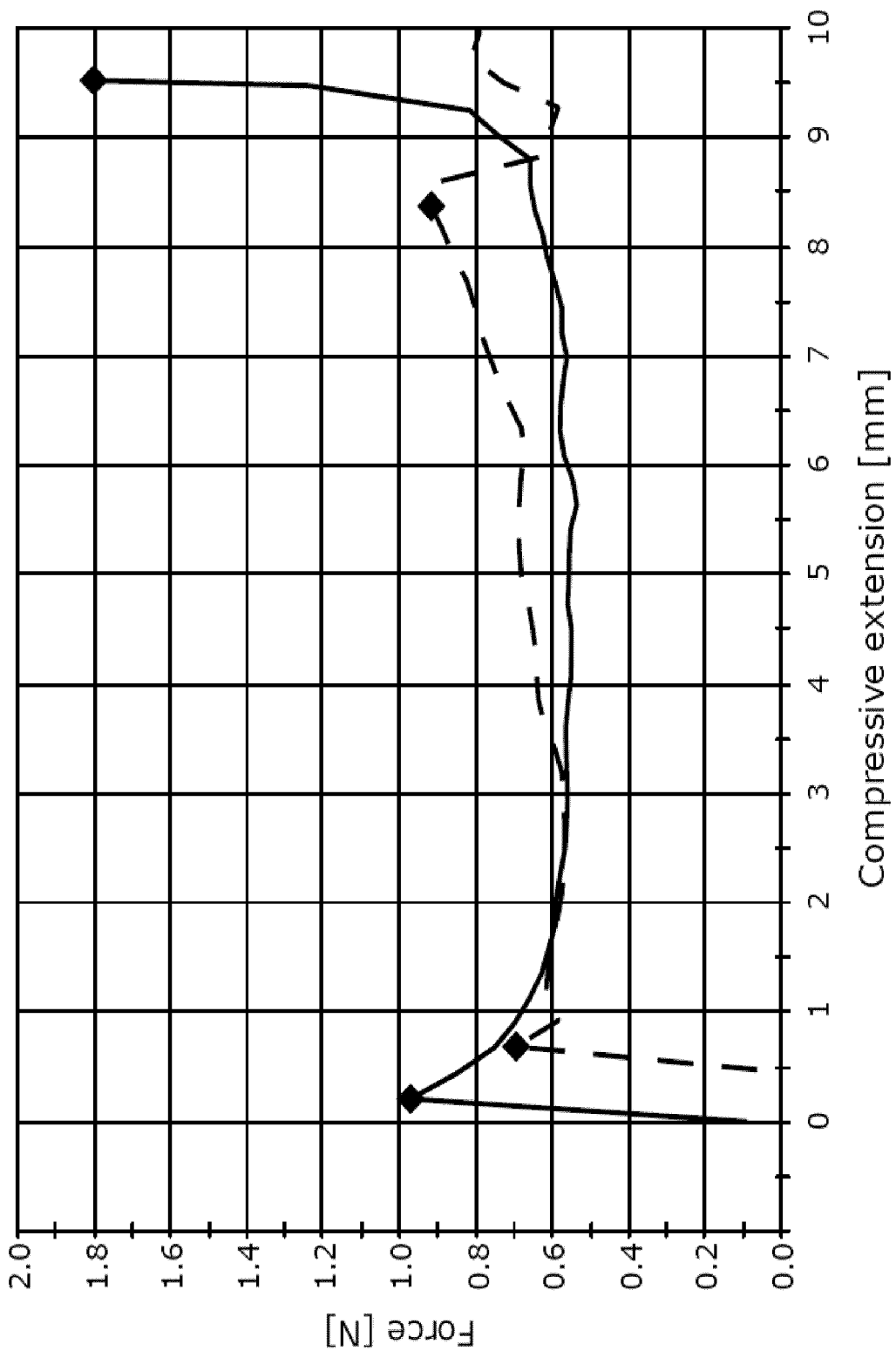
FIG. 4 shows an injectability plot of force (N) vs. compressive extension (mm) for the "development" injection vehicle as measured using the Instron device. Note that the y-axis scale differs from that of FIG. 3.
Figure 5:
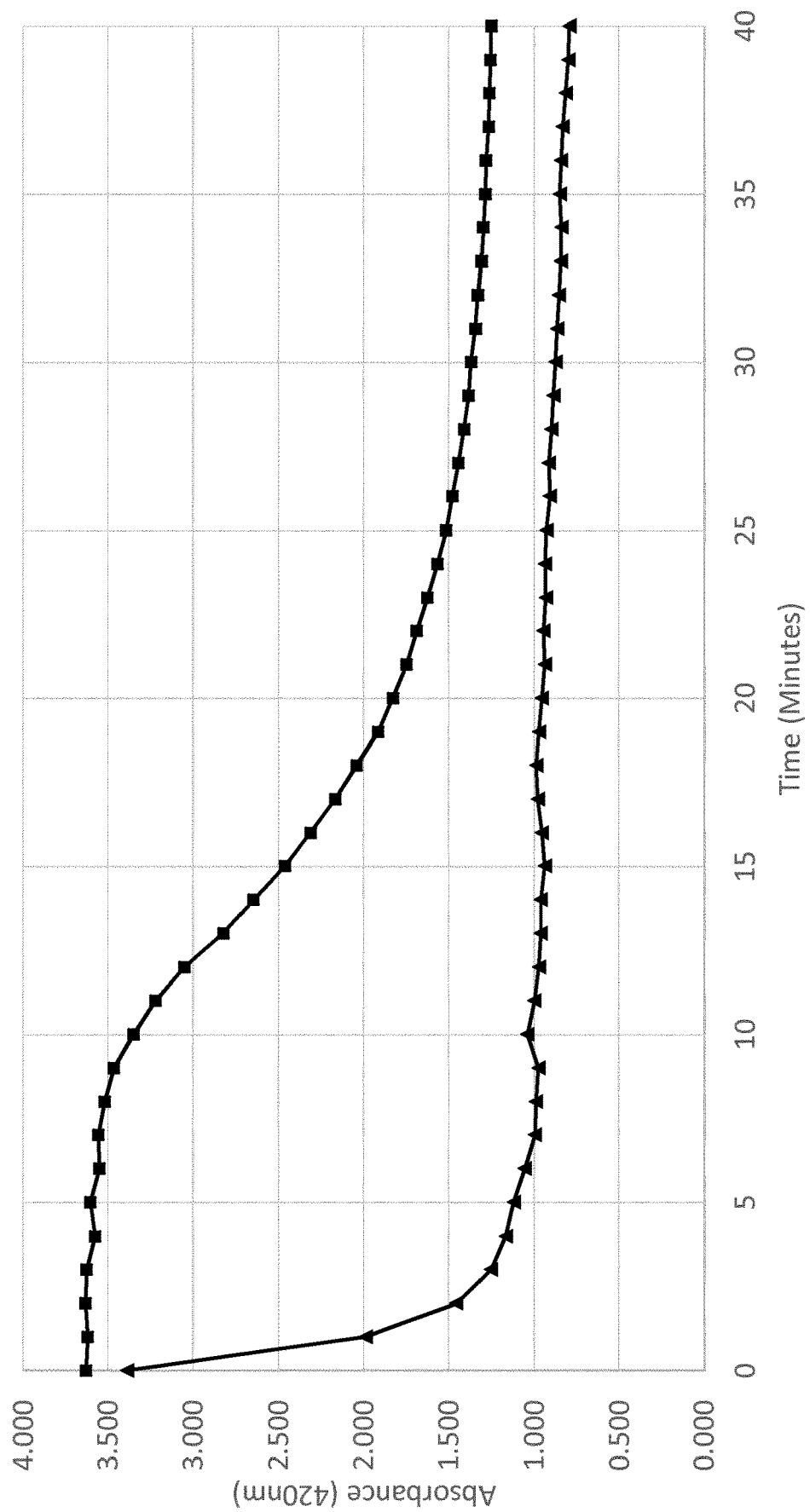
FIG. 5 shows a plot of sedimentation rate for the "current" (triangles) and "development" (squares) injection vehicle formulations as measured by the change in absorbance at 420 nm against time in minutes for a 17.5 mg/ml suspension of CsA-loaded microspheres in the respective injection vehicles.
Figure 6:
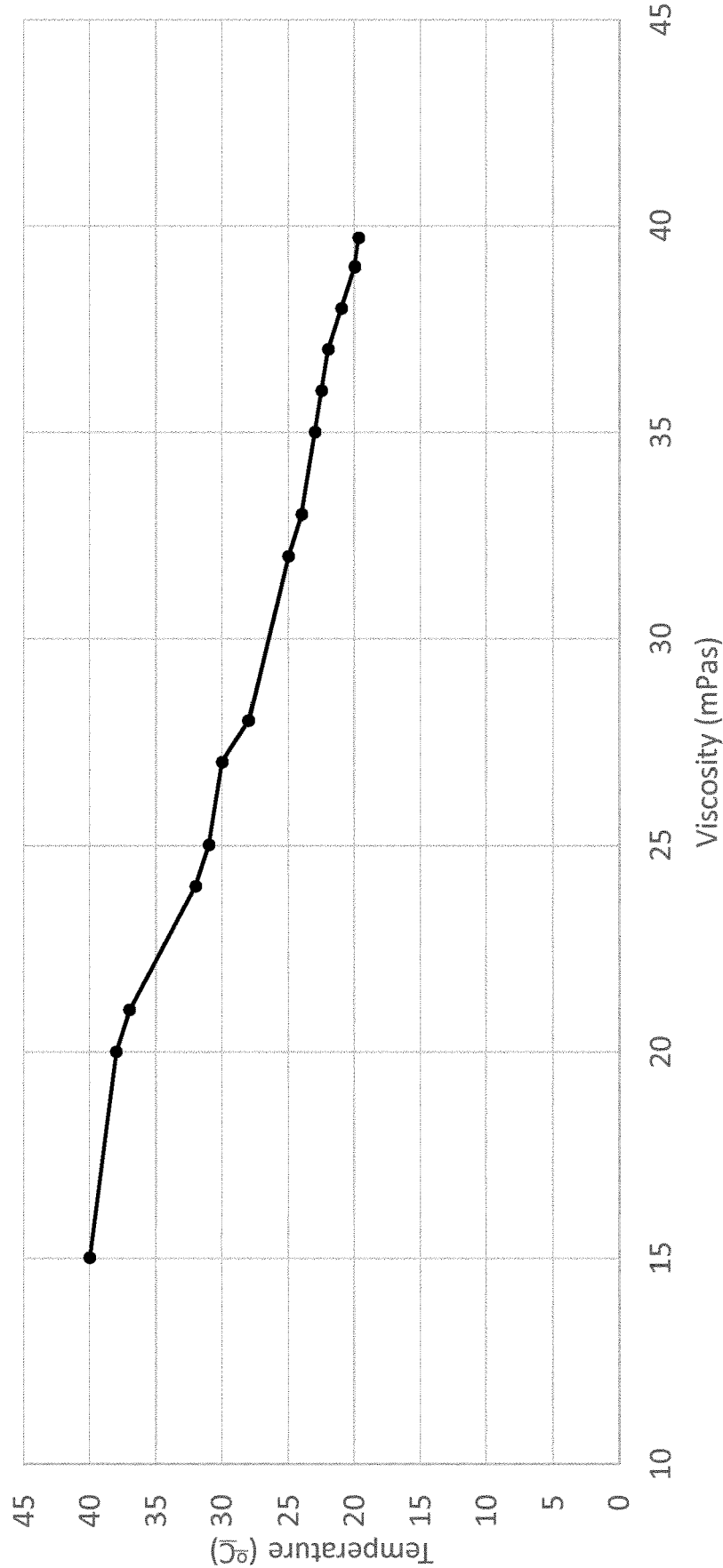
FIG. 6 shows a plot of temperature (° C.) vs. viscosity (mPas) for the "development" injection vehicle.

FIG. 2 shows uveitis disease severity scored by topical endoscopic fundal imaging (TEFI) over time in days for the above-described murine model of uveitis. Untreated (diamonds), vehicle treated by intravitreal injection (squares), treated with 4.5 µg cyclosporine (CsA) in the form of CsA-loaded microparticles of the invention (crosses) and treated with 6.7 mg/kg/day oral CsA (circles). Both CsA-treated groups exhibited lower TEFI score (i.e. less severe disease) than untreated or vehicle.

Example 5—Comparison of Injectability of Various Injection Vehicle Formulations

The present study aimed to identify an injection vehicle formulation with improved ease of wetting, improved suspension stability (i.e. longer time remaining in suspension before microparticles settle) and/or improved injectability.

The following injection vehicle formulations were prepared:

TABLE 11

Injection Vehicle Formulations

| Injection vehicle | Excipients | Concentration (mg/mL) | Density (g/mL) | Viscosity (mPas) |
|---|---|---|---|---|
| A | PBS | 6.5 | 1.012 | 2.84 |
| | Polysorbate 20 | 0.7 | | |
| | Carboxymethyl cellulose sodium | 5 | | |
| B | PBS | 6.5 | 1.010 | 6.16 |
| | Polysorbate 20 | 0.5 | | |
| | Hydroxyethyl cellulose | 2.5 | | |
| C | PBS | 6.5 | 1.004 | 2.55 |
| | Polysorbate 80 | 1 | | |
| | Carboxymethyl cellulose sodium | 5 | | |
| D | PBS | 6.5 | 0.965 | 21.6 |
| | Polysorbate 80 | 1 | | |
| | Hypromellose | 5 | | |
| | Disodium edetate | 1.3 | | |
| E | Sodium chloride | 8.5 | 1.012 | 1.35 |
| | Sucrose | 4.5 | | |
| | Polysorbate 20 | 0.5 | | |
| F | PBS | 6.5 | 0.984 | 51.3 |
| | Hypromellose | 5 | | |
| | Polysorbate 80 | 1 | | |
| | Poloxamer 407 | 2 | | |
| | Hydroxyethyl cellulose | 2.5 | | |
| G | PBS | 6.5 | 0.952 | 52.1 |
| | Hypromellose | 5 | | |
| | Polysorbate 80 | 1 | | |
| | Poloxamer 407 | 2 | | |
| | Hydroxyethyl cellulose | 2.5 | | |
| | Sucrose | 4.5 | | |
| | Disodium edetate | 1.3 | | |
| H | PBS | 6.5 | 0.967 | 29.7 |
| | Polysorbate 20 | 0.5 | | |
| | Hydroxyethyl cellulose | 2 | | |
| | Hypromellose | 4 | | |
| | Mannitol | 6 | | |
| I | PBS | 6.5 | 0.996 | 24.6 |
| | Polysorbate 20 | 0.5 | | |
| | Hydroxyethyl cellulose | 2 | | |
| | Hypromellose | 3 | | |
| | Mannitol | 5 | | |
| | Poloxamer 407 | 1 | | |
| | Disodium edetate | 1 | | |

Viscosity was measured using an A&D SV-1a Vibroviscometer (A&D Instruments Ltd, Abingdon, UK) according to the manufacturer's instructions. The A&D Vibro Viscometer instruction manual © 2008 is available from the A&D website.

Calibration with a sample of water @ 20° C. was performed before use. Sample volumes of 35-45 mL were used to determine viscosity. Viscosity readings are shown in Table 11 above and in Tables 12 and 13 below. All readings were taken at 20° C. unless specified otherwise.

An evaluation of reconstitution time, wettability and syringeability of the microparticles (50 mg microparticles in either 400 µl for 125 mg/mL or 333.3 µl for 150 mg/mL of injection vehicle) was carried out. Injection vehicles A, B, C and E were found to exhibit sub-optimal reconstitution and syringeability due to the fact that the microparticles tended to settle quickly, which in turn caused only or predominantly injection vehicle without microparticles to be drawn up into the syringe. Injection vehicles F and G were found to be too viscous leading to difficulty aspirating neat injection vehicle through 27G and 29G insulin syringes. Injection vehicles D, H and I exhibited the best reconstitution of microparticles into a homogeneous solution, and exhibited the best syringeability as assessed by 100 µl injection volume using either a fixed 27G or 29G insulin syringe. Based on reconstitution time, wettability, syringeability and quality of suspension, it was decided to combine injection vehicles D, H and I with the excipients and concentrations modified in order to produce a further injection vehicle formulation "J" (see Table 12 below). In addition to injection vehicle J, a replication injection vehicle formulation "K" was also made which differed from injection vehicle J by the addition of mannitol. This was done to test any difference that may be present following lyophilisation; mannitol would typically be added for microparticle formulations that are lyophilised prior to reconstitution.

TABLE 12

| Further Injection Vehicle Formulations | | | | |
|---|---|---|---|---|
| Injection vehicle | Excipients | Concentration (mg/mL) | Density (g/mL) | Viscosity (mPas) |
| J | PBS | 6.5 | 0.959 | 33.2 |
| | Polysorbate 80 | 1 | | |
| | Hydroxyethyl cellulose | 1.5 | | |
| | Hypromellose | 4.5 | | |
| K | PBS | 6.5 | 0.945 | 34.1 |
| | Polysorbate 80 | 1 | | |
| | Hydroxyethyl cellulose | 1.5 | | |
| | Hypromellose | 4.5 | | |
| | Mannitol | 5 | | |
| L | PBS | 6.5 | 0.952 | 40.2 at 17.4° C. |
| | Polysorbate 80 | 1.0 | | |
| | Hydroxyethyl cellulose | 2.0 | | |
| | Hypromellose | 4.0 | | |

Injection vehicles J and K were evaluated for reconstitution and wettability. 333.3 µl of each injection vehicle was added to 50 mg of microparticles to give 150 mg/mL. Reconstitution was facilitated by vortexing for approx. 3 mins and sonicating for approx. 3 mins. The resulting suspension was found to be highly homogeneous. Syringeability of injection vehicles J and K was confirmed using the Instron device with a 100 µl injection volume and a fixed 27G insulin syringe. Both injection vehicles J and K exhibited similar results (injectability achieved 2 out of 3 attempts), suggesting that presence or not of mannitol does not significantly alter syringeability of the injection vehicle.

Further optimization of the injection vehicle formulation led to injection vehicle L (see Table 12 above), which was used for further development. The properties of an earlier injection vehicle formulation ("current") and of injection vehicle L ("development") are shown in Table 13 below.

TABLE 13

| Injection Vehicle Formulation Properties | | | | | |
|---|---|---|---|---|---|
| Injection vehicle | Excipients | Concentration (mg/mL) | Density (g/mL) | Viscosity (mPas) | pH |
| Current | PBS | 10.0 | 1.012 | 3.3 at 17.2° C. | 7.2 |
| | Polysorbate 20 | 0.4 | | | |
| | Carboxymethylcellulose sodium | 5.0 | | | |
| Development "L" | PBS | 6.5 | 0.952 | 40.2 at 17.4° C. | 7.3 |
| | Polysorbate 80 | 1.0 | | | |
| | Hydroxyethyl cellulose | 2.0 | | | |
| | Hypromellose | 4.0 | | | |

The injection vehicle formulations shown in Table 13 were tested for injectability using an Instron device. The concentration of CsA-loaded microparticles in both formulations was 150 mg/ml. The needle was 27G and the injection volume was 100 µl.

FIG. 3 shows a plot for the current injection vehicle formulation of force (N) vs. compressive extension (mm). FIG. 4 shows a plot for the development injection vehicle formulation of force (N) vs. compressive extension (mm). Noting the difference in y-axis scale for FIGS. 3 and 4, it is apparent that the development injection vehicle formulation achieved similar levels of compressive extension with around 10-fold lower force. This result was surprising because, as shown in Table 13, the development injection vehicle formulation actually has higher viscosity than the current injection vehicle formulation.

The sedimentation rates of the current and development injection vehicle formulations were evaluated by measuring the change in absorbance at 420 nm over time for a 17.5 mg/ml suspension of CsA-loaded microspheres in the current and development formulations, respectively. The results are shown in FIG. 5. As is readily apparent from FIG. 5, the current injection vehicle formulation exhibited much more rapid sedimentation than the development formulation (current showing substantial sedimentation in 1 minute vs. around 10-30 minutes for the development formulation).

Without wishing to be bound by any particular theory, the present inventors believe that the higher viscosity of the development injection vehicle formulation in comparison with the current formulation, and the correspondingly longer settling time, means that the microparticles are better-retained in suspension by the development formulation during the process of injection. It is thought that sedimentation of microparticles during injection may lead to aggregation of microparticles, which in turn results in "plug" formation that partially blocks the narrow needle required for intravitreal injection. This would explain the counter-intuitive finding, described above, that the more viscous development formulation requires less force to achieve a given level of compressive extension.

Lower levels of force to achieve a given injection volume through a narrow needle for intravitreal injection (e.g. 27G or 30G) are highly desirable. Accordingly, the development injection vehicle formulation is expected to provide improved injectability of CsA-loaded microparticles for intravitreal injection. Again, without wishing to be bound by any particular theory, the present inventors believe that the addition of the thixotropic agent hypromellose (also known as hydroxypropyl methylcellulose, "HPMC" or E464) contributes to the advantageous properties of the development injection vehicle formulation. The presence of a thixotropic agent in the injection vehicle results in a fluid that exhibits shear-thinning. In rheology, shear-thinning is the non-Newtonian behaviour of fluids whose viscosity decreases under shear strain. Again, without wising to be bound by any particular theory, the present inventors believe that an injection vehicle that exhibits shear-thinning is particularly advantageous in connection with the present invention. The relatively high viscosity in the absence of shear stress helps to maintain the microparticles in suspension. Injection through the narrow needle (e.g. for intravitreal injection) induces a shear stress that causes the viscosity of the shear-thinning fluid to drop, which facilitates injection. Therefore, it is specifically contemplated herein that the injection vehicle may comprise one or more thixotropic agents. Examples of thixotropic agents for use in the injection vehicle include: hypromellose, hydroxyethyl cellulose, hydrophillically-modified hydroxyethyl cellulose, Xanthan Gum, Guar Gum, and Cetyl alcohol.

All references cited herein are incorporated herein by reference in their entirety and for all purposes to the same extent as if each individual publication or patent or patent application was specifically and individually indicated to be incorporated by reference in its entirety.

The specific embodiments described herein are offered by way of example, not by way of limitation. Any sub-titles herein are included for convenience only, and are not to be construed as limiting the disclosure in any way.

The invention claimed is:

1. A controlled release pharmaceutical formulation for intravitreal injection, comprising cyclosporine-loaded microparticles, said microparticles comprising at least one bioresorbable polymer comprising poly(D,L-lactide), wherein the mean diameter of the microparticles ranges from 20 μm to 40 μm as measured by electron microscopy, and wherein the formulation comprises said microparticles suspended in a liquid vehicle, which liquid vehicle has a viscosity from 30 mPas to 45 mPas as measured at 20° C. using a vibrational viscometer in the absence of said cyclosporine-loaded microparticles, and wherein the formulation further comprises a thixotropic agent selected from the group consisting of hypromellose, hydroxyethyl cellulose, hydrophillically-modified hydroxyethyl cellulose, xanthan gum, guar gum, cetyl alcohol and a combination thereof, and wherein the liquid formulation exhibits shear-thinning behaviour such that the viscosity is lower under the shear strain of intravitreal injection than in the absence of said shear strain.

2. The formulation according to claim 1, wherein said microparticles comprise a blend of bioresorbable polymers, wherein said blend comprises said poly(D,L-lactide) polymer in combination with poly(L-lactide), or poly(D,L-lactide-co-glycolide), or a mixture thereof.

3. The formulation according to claim 2, wherein said blend of bioresorbable polymers comprises between 1% and 15% w/w of poly(L-lactide).

4. The formulation according to claim 1, wherein said microparticles comprise 15% to 25% w/w of cyclosporine.

5. The formulation according to claim 1, wherein at least 95% of the microparticles of the formulation have a diameter from 25 μm to 40 μm, as measured by electron microscopy.

6. The formulation according to claim 1, wherein the formulation further comprises a pharmaceutically acceptable carrier, diluent, buffer, anti-agglomeration agent and/or viscosity modifier.

7. The formulation according to claim 6, wherein the pharmaceutically acceptable carrier or diluent comprises a salt, or a sugar, or sterile water, or a combination thereof.

8. The formulation according to claim 1, further comprising a component selected from the group consisting of polysorbate 20, polysorbate 80, phosphate buffered saline, sucrose, carboxymethyl cellulose, mannitol, and a combination thereof.

9. The formulation according to claim 8, wherein the formulation comprises phosphate buffered saline, polysorbate 80, hydroxyethyl cellulose and hypromellose.

10. The formulation according to claim 9, wherein the concentration of the following components are in the respective concentration ranges as follows:
phosphate buffered saline: 5.0 mg/mL to 8.0 mg/mL;
polysorbate 80: 0.8 mg/mL to 1.2 mg/mL;
hydroxyethyl cellulose: 1.8 mg/mL to 2.2 mg/mL;
hypromellose: 3.8 mg/mL to 4.2 mg/mL; and
said cyclosporine-loaded microparticles: 100 mg/mL to 200 mg/mL.

11. The formulation according to claim 1, wherein the formulation is in injectable form or wherein said microparticles and said liquid vehicle are reconstituted into injectable form by mixing prior to use.

12. The formulation according to claim 11, wherein the formulation is for intravitreal depot injection.

13. The formulation according to claim 6, wherein the formulation is injectable through a 30 gauge, 0.5 inch length hypodermic needle at a recovery percentage of at least 80%.

14. A method of treating uveitis in a mammalian subject, comprising administering by intravitreal injection a controlled release pharmaceutical formulation as defined in claim 1 to the subject in need of therapy.

15. The method according to claim 14, wherein the uveitis is sight-threatening intermediate, posterior or pan-uveitis of non-infectious aetiology, or wherein the uveitis is equine recurrent uveitis.

16. The method according to claim 15, wherein the treatment is reduction or prevention of uveitis recurrence in a subject undergoing steroidal uveitis treatment.

17. The method according to claim 14, wherein the uveitis is sight threatening tuberculosis uveitis.

18. The method according to claim 17, wherein the method further comprises administering antibiotic therapy to the subject for treatment of tuberculosis infection.

19. A process for producing an injectable formulation of cyclosporine-loaded microparticles as defined in claim 1, comprising:
providing a dry population of said cyclosporine-loaded microparticles;
bringing the microparticles into contact with an injection vehicle solution comprising: phosphate buffered saline, polysorbate 80, hydroxyethyl cellulose and hypromellose, wherein said injection vehicle has a viscosity from 30 mPas to 45 mPas as measured at 20° C. using a vibrational viscometer, and wherein the liquid formulation exhibits shear-thinning behaviour such that the viscosity decreases under shear strain.

20. The process according to claim 19, wherein the concentration of the following components are combined in the respective concentration ranges as follows:
- phosphate buffered saline: 5.0 to 8.0 mg/mL;
- polysorbate 80: 0.8 to 1.2 mg/mL;
- hydroxyethyl cellulose: 1.8 to 2.2 mg/mL;
- hypromellose: 3.8 to 4.2 mg/mL; and
- said cyclosporine-loaded microparticles: 100 to 200 mg/mL.

21. The formulation according to claim 9, wherein the formulation further comprises mannitol.

22. The formulation according to claim 21, wherein the concentrations of the following components are in the respective concentration ranges as follows:
- phosphate buffered saline: 5.0 mg/mL to 8.0 mg/mL;
- polysorbate 80: 0.8 mg/mL to 1.2 mg/mL;
- hydroxyethyl cellulose: 1.8 mg/mL to 2.2 mg/mL;
- hypromellose: 3.8 mg/mL to 4.2 mg/mL;
- mannitol, 4.8 mg/mL to 5.2 mg/mL; and
- said cyclosporine-loaded microparticles: 100 mg/mL to 200 mg/mL.

23. The process according to claim 19, wherein the injection vehicle solution comprises mannitol.

24. The process according to claim 23, wherein the concentration of the following components are combined in the respective concentration ranges as follows:
- phosphate buffered saline: 5.0 mg/mL to 8.0 mg/mL;
- polysorbate 80: 0.8 mg/mL to 1.2 mg/mL;
- hydroxyethyl cellulose: 1.8 mg/mL to 2.2 mg/mL;
- hypromellose: 3.8 mg/mL to 4.2 mg/mL;
- mannitol: 4.8 mg/mL to 5.2 mg/mL; and
- said cyclosporine-loaded microparticles: 100 mg/mL to 200 mg/mL.

25. The formulation according to claim 1, wherein said liquid vehicle comprises a salt, or a sugar, or sterile water, or a combination thereof.

26. The formulation according to claim 1, wherein the concentration of cyclosporine-loaded microparticles is at least 100 mg/mL.

27. The formulation according to claim 6, wherein the pharmaceutically acceptable carrier, or diluent comprises a surfactant.

28. The formulation according to claim 1, wherein the liquid vehicle comprises a surfactant.

* * * * *